United States Patent
Hunter et al.

[11] Patent Number: 5,922,204
[45] Date of Patent: *Jul. 13, 1999

[54] METHOD AND APPARATUS FOR BIOREMEDIATION OF MIXED HAZARDOUS WASTES

[76] Inventors: Robert M. Hunter; Frank M. Stewart, both of 320 S. Willson Ave., Bozeman, Mont. 59715

[*] Notice: This patent is subject to a terminal disclaimer.

[21] Appl. No.: 07/926,047

[22] Filed: Aug. 4, 1992

[51] Int. Cl.[6] .............................. C02F 3/28; C02F 11/04
[52] U.S. Cl. ..................... 210/603; 210/605; 210/610; 210/614; 210/631; 210/630; 210/747; 435/262.5
[58] Field of Search .................... 210/610, 603, 210/605, 614, 631, 747, 630; 435/262.5

[56] References Cited

U.S. PATENT DOCUMENTS

| | | | |
|---|---|---|---|
| 4,022,665 | 5/1977 | Ghosh et al. | 195/27 |
| 5,037,551 | 8/1991 | Barkley et al. | 210/603 |
| 5,196,121 | 3/1993 | Moore et al. | 210/603 |
| 5,232,596 | 8/1993 | Castaldi | 210/603 |
| 5,246,584 | 9/1993 | Donaldson et al. | 210/603 |
| 5,277,815 | 1/1994 | Beeman | 210/605 |
| 5,342,769 | 8/1994 | Hunter et al. | 210/605 |
| 5,441,887 | 8/1995 | Hanson et al. | 435/262.5 |

OTHER PUBLICATIONS

Egli et al, "Anaerobic dechlorination of tetrachloromethane and 1,2,–dichloromethan . . . " FEMS Microbiology Letters, 43 (1987) 257–261.

Primary Examiner—Thomas M. Lithgow
Attorney, Agent, or Firm—Robert M. Hunter

[57] ABSTRACT

A method and apparatus for bioremediation of mixed hazardous waste is discussed. The method and apparatus can be used for treatment of a liquid or slurry hazardous waste stream (e.g., industrial wastewater or sludge) or for treatment of contaminated groundwater. Removal of the following constituents is possible: (1) aromatic hydrocarbons, such as benzene, toluene, ethylbenzene, xylenes, phenols and cresols, (2) halogenated (e.g., chlorinated) hydrocarbons, such as tetrachloroethylene, trichloroethylene, 1,1,1-trichloroethane and similar xenobiotics, (3) heavy metals, such as copper, lead, zinc, lead, mercury, cadmium, and chromium, (4) acids, such as sulfuric acid and nitric acid, and (5) salts, such as sulfates and nitrates. One embodiment of the invention involves the steps of denitrification (e.g., nitrate reduction), sulfate reduction, methanogenesis and aerobic respiration. Other embodiments delete the denitrification, sulfate-reduction or aerobic respiration steps. In a preferred embodiment, at least a portion of the denitrification and/or sulfate-reduction steps occur in a suspended continuous culture reactor under kinetic control, while the methanogenesis may occur in a biofilm (e.g., in a packed bed reactor or in situ underground.) Reductive dechlorination, control of pH, energy conservation and control of air pollution are accomplished.

34 Claims, 3 Drawing Sheets

METHOD AND APPARATUS FOR BIOREMEDIATION OF MIXED HAZARDOUS WASTES

This invention was made with Government support under Contract No. DAAH01-922-C-R068 awarded by the Defense Advanced Research Projects Agency, a component of the U.S. Department of Defense. The Government has certain rights in the invention.

TECHNICAL FIELD

This invention relates to a method and apparatus for bioremediation of mixed hazardous wastes and, more particularly, to a method and apparatus that uses enrichment means, including kinetic control, to create a biomimetic process for hazardous waste remediation.

It is described in detail in a report entitled "Biomimetic Process for Hazardous Waste Remediation" by Yellowstone Environmental Science, Inc., 320 S. Willson Ave., Bozeman, Mont. 59715.

BACKGROUND

The activities of U.S. Department of Defense (DoD) and its contractors result in the generation of large amounts of hazardous wastes. Many of the constituents of concern are waterborne or have become waterborne as a result of leaks or spills. Among the most troublesome of these wastes are organic solvents, heavy metals, acids and salts. Even at low concentrations, these constituents are often toxic, tend to be resistant to conventional treatment methods and are persistent in the environment. Common waste constituents include the following:

Aromatic hydrocarbons
- benzene
- toluene
- ethylbenzene
- xylenes
- phenols
- cresols Halogenated hydrocarbons
- tetrachloroethylene (PCE)
- trichloroethylene (TCE)
- 1,1,1-trichloroethane (TCA)

Heavy metals

Inorganic acids and salts

Benzene, toluene and xylenes are components of fuels and often the focus of groundwater cleanup efforts. Phenols and cresols are used in paint stripping and carbon (smut) removal operations. Halogenated hydrocarbons are used as solvents and in vapor degreasing operations. Heavy metals, acids and inorganic salts are present in metal stripping and electroplating effluents.

In liquid wastewater streams, in sludges and in contaminated groundwater, the above constituents are often found together. It is appropriate, then, to seek remediation processes that handle mixed hazardous waste streams.

NATURE OF THE INVENTION

The present invention provides a method and apparatus for bioremediation of mixed hazardous wastes. The invention is an application of the concept of kinetic control as disclosed in Robert M. Hunter's U.S. Pat. No. 5,076,927, which patent is incorporated herein in its entirety by reference.

The present method and apparatus incorporate a series of reactors in which treatment process steps are accomplished. The process disclosed herein enriches in one or more reactors a particular microorganism or consortia that is capable of accomplishing the hazardous waste transformations sought. An enrichment culture can be described as follows:

"A culture medium of defined chemical composition . . . inoculated with a mixed population of microorganisms . . . and incubated under defined cultural conditions. Those microorganisms best adapted to the given environment . . . are selected (i.e., favored) and finally predominate. Conversely, those microorganisms poorly adapted to the conditions provided are counter-selected (i.e., disfavored) and either disappear or become a minority component of the mature enrichment culture." (Stolp H. and Starr, M. P. Principles of isolation, cultivation, and conservation of bacteria. In M. P. Starr, H. Stolp, H. G. Truper, A. Balows, and H. G. Schlegal (Eds.), *The Prokarvotes* (volume I) 948–977, New York: Springer-Verlag, 1981) While enrichment can be accomplished in a variety of ways, this invention primarily uses "kinetic control" of continuous cultures as an "open system" selection mechanism. With kinetic control, growth rate (dilution rate or mean cell residence time) is used to favor particular microorganisms and disfavor others. In general, it involves operation of serial continuous cultures at successively lower dilution rates. If cell recycle is practiced, the downstream reactor(s) are operated at a greater mean cell residence times (MCRT) than upstream reactor(s). This enrichment technique can be used to enrich in an upstream reactor microorganisms or consortia that are capable of more rapid growth than those enriched in a downstream reactor.

A practical limitation of use of kinetic control for enrichment purposes is that good engineering practice in design of treatment processes requires that a safety factor be applied to the minimum MCRT shown to be effective in a laboratory setting. It is recommended that a design MCRT should be two to ten times the minimum MCRT that causes washout of the desired microorganisms. Thus, from a practical perspective, use of kinetic control is feasible only in those situations wherein the maximum specific growth rates ($\mu_{max}$) of organisms to be separated differ by a factor of 2–10.

In addition to kinetic control, the invention uses other factors to impose selection pressures on the mixed cultures that continuously inoculate the open systems disclosed herein. A second fundamental factor is the oxidation-reduction potential (ORP) of the culture medium. In this regard, three different conditions are used: aerobic, anoxic and anaerobic. Under aerobic conditions, dissolved molecular oxygen ($O_2$) is present. Under anoxic conditions, $O_2$ is substantially absent. Under anaerobic conditions, a substantially negative (e.g., −200 millivolts) oxidation reduction potential (ORP) exists in the medium.

A third factor that is used as an enrichment means is available limiting substrate. A limiting substrate is one that is available in a growth-limiting amount relative to other medium components. In the absence of easily degraded substrates, the availability of a xenobiotic limiting substrate effectively selects for microorganisms capable of its metabolism. In the instance of cometabolism, the primary substrate (the substrate fueling growth, be it electron donor or electron acceptor) is used as the limiting substrate.

A fourth factor is medium temperature. In general, three temperature ranges are used: room temperature=20–25° C., mesophilic temperature=30–40° C. and thermophilic temperature=50–60° C.

One preferred embodiment of the method and apparatus involves four reactors operated in series. A mixed culture of denitrifying (e.g., nitrate-reducing) bacteria is enriched in the first reactor; a mixed culture of sulfate-reducing bacteria is enriched in the second reactor; a mixed culture of methanogenic bacteria is enriched in the third reactor; and a mixed culture of aerobic microorganisms is enriched in the fourth reactor.

The first step in this embodiment of the process involves delivering to the first reactor an aqueous waste stream or slurry that contains mixed hydrocarbons as well as nitric acid ($HNO_3$) and sulfuric acid ($H_2SO_4$). Both nitric acid and sulfuric acid are "oxy" acids in that they are compounds that comprise oxygen. The disassociated forms of these acids, nitrate and sulfate, are "oxyanions." The term "mixed hydrocarbons" means aromatic hydrocarbons and/or halogenated hydrocarbons. Examples of aromatic hydrocarbons include benzene, toluene, ethylbenzene, xylenes, phenols and cresols. Examples of halogenated hydrocarbons include tetrachloroethylene (PCE), trichloroethylene (TCE), and 1,1,1-trichloroethane (TCA). Gaseous and dissolved molecular oxygen is excluded from the first reactor so as to create an anoxic environment. Molecular oxygen is excluded from the first reactor by constructing the reactor of materials that are substantially impermeable to oxygen, by excluding oxygen from any gases introduced to the reactor for purging or mixing purposes and by ensuring that the aqueous waste stream includes sufficient biochemical oxygen demand. In a preferred embodiment, the contents of the reactor are completely mixed and operated at a substantially constant (±2° C.) temperature and at substantially constant (±0.2 units) pH and denitrifying bacteria are grown in the reactor in suspended continuous culture. If necessary, a supplemental source of a nitrogen oxide (such as nitrate ion, nitrite ion, nitric oxide or nitrous oxide) is added to the reactor.

In a preferred embodiment, the first reactor is operated as a completely mixed continuous stirred tank reactor (CSTR) with or without cell recycle at a predetermined dilution rate or mean cell residence time that enriches in the reactor a mixed culture that includes denitrifying bacteria, but that washes out substantially all (95+percent) sulfate-reducing bacteria and methanogenic bacteria. At least a portion of the mixed hydrocarbons present in the waste stream serve as the substrate, carbon source and electron donor for denitrifying bacteria. In an alternative embodiment, an alternative primary substrate, such as methanol or acetate, is added and the mixed hydrocarbons act as supplemental substrates during cometabolism. A nitrogen oxide (such as nitrate ion formed by disassociation of nitric acid) serves as the electron acceptor.

During the denitrification step, at least a portion of the mixed hydrocarbons are metabolized and the nitrogen oxide is reduced (in part to nitrogen gas.) At least a portion of the metals dissolved in the waste stream is precipitated as metal hydroxides and may be separated from the liquid effluent of the reactor. Similarly, the nitrogen gas may be separated from the liquid effluent of the first reactor by imposing a vacuum on the headspace of the first reactor. Alternatively, if a small amount of nitrogen gas is produced, it is not separated from the liquid effluent of the first reactor. In an alternative embodiment, nitrogen gas separated from the liquid effluent of the first reactor is used to purge the second reactor to facilitate removal of hydrogen sulfide.

In this embodiment, the liquid effluent from the first reactor is transferred to a second reactor, wherein the second process step is accomplished. An anaerobic environment is created in the second reactor in the same way that an anoxic environment is created in the first reactor. In a preferred embodiment, the contents of the reactor are completely mixed and operated at a predetermined, substantially constant temperature and pH and sulfate-reducing bacteria are grown in the reactor in suspended continuous culture. If necessary, a supplemental source of sulfate ion (such as sulfuric acid) is added to the reactor.

In a preferred embodiment, the second reactor is operated as a completely mixed continuous stirred tank reactor (CSTR) with or without cell recycle at a predetermined dilution rate or mean cell residence time that enriches in the reactor a mixed culture of sulfate-reducing bacteria, but that washes out substantially all (95+ percent) methanogenic bacteria. At least a portion of the mixed hydrocarbons remaining in the waste stream serve as the substrate, carbon source and electron donor for sulfate-reducing bacteria. Sulfate serves as the primary electron acceptor, but halogenated hydrocarbons may also serve as electron acceptors. During the sulfate-reduction step, at least a portion of the mixed hydrocarbons are metabolized and the sulfate is reduced to form hydrogen sulfide gas. Reductive dehalogenation (e.g., dechlorination or debromination) of at least a portion of the halogenated hydrocarbons occurs. Metals dissolved in the waste stream are precipitated as metal sulfides and may be separated from the liquid effluent of the second reactor. Similarly, excess hydrogen sulfide gas is separated from the liquid effluent of the second reactor, if necessary to lower the hydrogen sulfide concentration of the effluent below the level that is toxic to methanogenic bacteria. Separation of hydrogen sulfide gas may be achieved by purging the second reactor with an oxygen-free gas, such as nitrogen, by imposing a vacuum on the headspace of the reactor or by precipitating the sulfide with an iron salt. If the hydrogen sulfide is removed by purging or vacuum techniques, sulfur can be recovered from the gas using the Claus process or the biotechnology disclosed in U.S. Pat. No. 4,666,852, which patent is incorporated herein by reference.

In this embodiment, the liquid effluent from the second reactor is transferred to a third reactor, wherein the third process step is accomplished. An anaerobic environment is maintained in the third reactor. The contents of the third reactor may or may not be completely mixed by recirculation or other means. Methanogenic bacteria (which biologically produce methane) are grown in either suspended continuous culture or on biofilms or in both ways. The biofilms may be in a fixed-film reactor, such as a packed bed reactor. Alternatively, if contaminated groundwater is being treated, the methanogenic step may occur, at least in part, in biofilms that colonize the pore space of a porous underground formation after the effluent is reinjected into the ground. The reactor is operated at substantially constant temperature and pH.

In a preferred embodiment, the third reactor is operated as a completely mixed continuous stirred tank reactor (CSTR) with or without cell recycle at a predetermined dilution rate or mean cell residence time that enriches in the reactor a mixed culture that includes methanogenic bacteria. At least a portion of the breakdown products of denitrification and sulfate reduction are converted to methane gas in the third reactor. Reductive dehalogenation (e.g., dechlorination) of at least a portion of the remaining halogenated hydrocarbons also occurs. Methane gas is separated from the liquid effluent of the third reactor.

Methane is a saturated hydrocarbon and an alkane. During methane synthesis by methanogenic bacteria, reductive dehalogenation of halogenated hydrocarbons occurs. One end product of reductive dechlorination of such chlorinated hydrocarbons as PCE and TCE is ethylene. Ethylene is an unsaturated hydrocarbon and an alkene.

In some embodiments, the methane gas is used as fuel in internal combustion engines used to drive process-related pumps and generate waste heat or is burned to generate waste heat. Waste heat is used to heat the reactors and their contents.

In one embodiment, the liquid effluent from the third reactor is transferred to a fourth reactor, wherein the fourth process step is accomplished. An aerobic environment is maintained in the fourth reactor by introducing molecular oxygen or air to the reactor contents. The contents of the fourth reactor may or may not be completely mixed. Aerobic microorganisms are grown in either suspended continuous culture or on biofilms. Mineralization of remaining organic waste constituents occurs and the effluent from the process may be released to the environment.

In a second preferred embodiment of the method and apparatus, only two of the above process steps are practiced: the denitrification step and the methanogenic step. The same operating conditions are used for each step, with denitrification occurring prior to methanogenesis.

In a third preferred embodiment of the method and apparatus, another two of the above process steps are practiced: the sulfate-reduction step and the methanogenesis step. The same operating conditions are used for each step, with sulfate reduction occurring prior to methanogenesis. Some embodiments of the invention constitute a new use of the method disclosed in U.S. Pat. No. 5,076,927. Details of the methods incorporated in U.S. Pat. No. 5,076,927 are presented in Robert M. Hunter's 1989 Montana State University doctoral thesis entitled "Biocatalyzed Partial Demineralization of Acidic Metal Sulfate Solutions", which thesis is available from University Microfilms International, 300 North Zeeb Road, Ann Arbor, Mich. 48106-1346 as Order No. 9019886.

It is an object of the invention to provide a multistep process for treatment of mixed hazardous waste streams. It is an object of the invention for an initial denitrification step and/or a sulfate-reduction step to protect a downstream methanogenic step from inhibition by heavy metal toxicity. This is important because the presence of low concentrations of heavy metals (Cu, Hg, Zn, Cd and Cr) has been shown to significantly inhibit biodegradation of at least one "benchmark" xenobiotic compound (2,4-DME). It is a further object of the invention for an initial denitrification step and/or a sulfate-reduction step to protect a downstream methanogenic step from inhibition by wide pH swings. It is a further object of the invention for metabolism of some aromatic hydrocarbons in a denitrification step and/or a sulfate-reduction step to produce carbon dioxide, hydrogen and volatile acids which are converted to methane in a subsequent process step.

Another object of the invention is to conserve energy in that anoxic and anaerobic process steps do not require (energy intensive) aeration. A methanogenic step would produce biogas that can be used to maintain appropriate reactor temperatures. Another object of the invention is to prevent air pollution in that loss of volatile hydrocarbons to the atmosphere (as often occurs with aerobic treatment processes) does not occur. If sulfur is recovered from the waste hydrogen sulfide gas stream, the only gaseous products released to the environment are nitrogen and carbon dioxide, as methane ($CH_4$) and ethylene are oxidized during the use (e.g., combustion) of biogas. Another object of the invention is to minimize waste sludge production in that, compared to aerobic processes, very little biomass (waste sludge) is produced. It is another object of the invention to remove all cresol isomers (meta, ortho, and para) in the sulfate-reduction step, via syntrophic utilization of these substrates. It is another object of the invention that reductive dehalogenation of halogenated hydrocarbons occurs in both anaerobic process steps. Further objects and advantages of the invention will become apparent from a consideration of the drawings and ensuing description of them.

BRIEF DESCRIPTION OF THE DRAWINGS

These features will be better understood by reference to the accompanying drawings which illustrate presently preferred embodiments of the invention.

In the drawings.

DETAILED DESCRIPTION OF THE INVENTION

Figure 1:
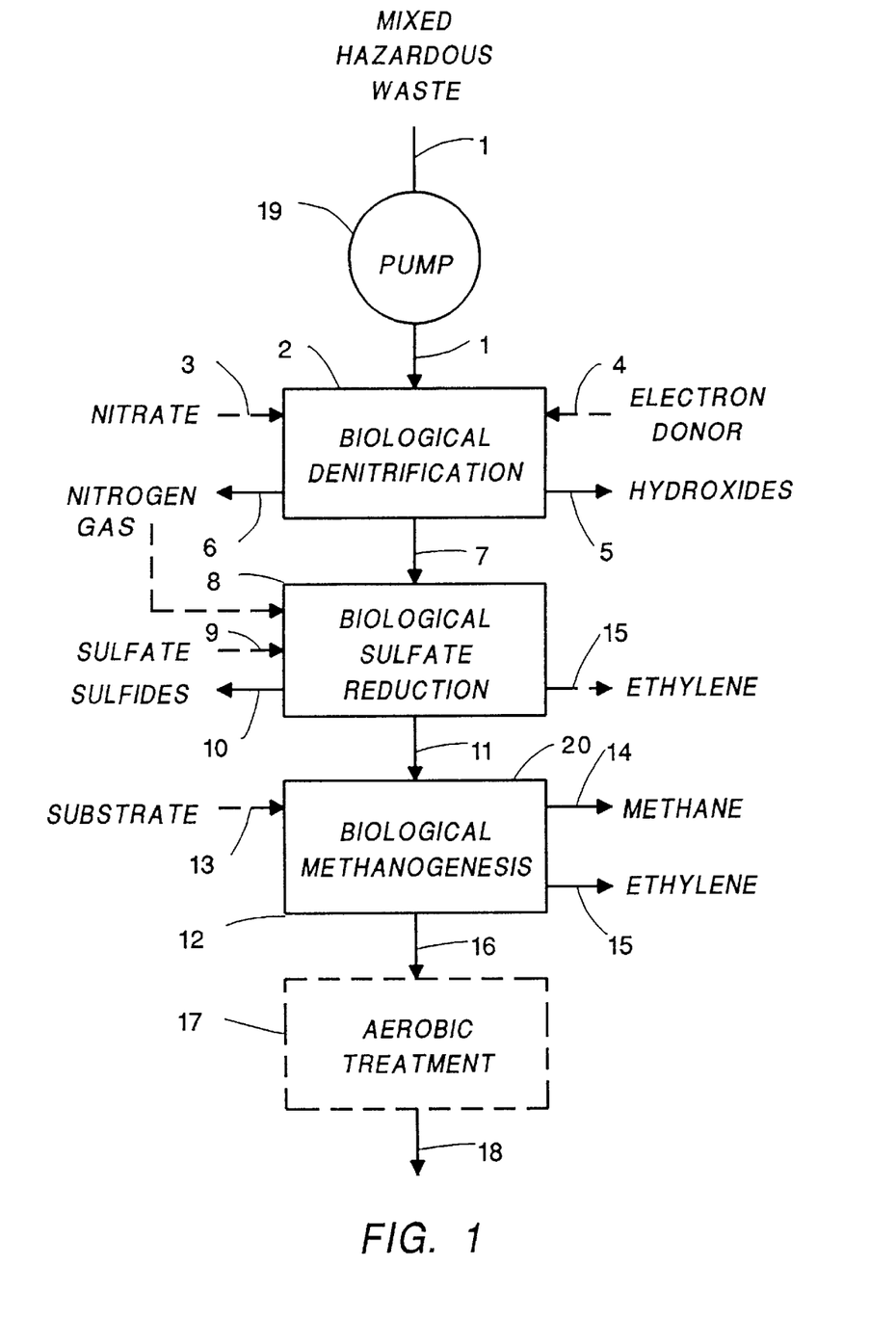
FIG. 1 is a schematic diagram of a first preferred embodiment of the invention.

Reference is now made to FIG. 1 which is a highly schematic block diagram illustrating a first preferred embodiment of the invention, the dashed lines representing possible variations in the process. Mixed hazardous waste 1 is the primary input to the process. Mixed hazardous waste means aromatic hydrocarbons and/or halogenated hydrocarbons, heavy metals, acids and salts. Examples of aromatic hydrocarbons include benzene, toluene, ethylbenzene, xylenes, phenols and cresols. Examples of halogenated hydrocarbons include tetrachloroethylene (PCE), trichloroethylene (TCE), and 1,1,1-trichloroethane (TCA). Examples of heavy metals include copper, lead, zinc and mercury. Examples of acids include nitric acid, sulfuric acid and hydrochloric acid. Examples of salts include sodium nitrate, sodium sulfate and sodium chloride.

A first preferred embodiment of the method and apparatus which is appropriate for processing a mixed waste stream involves an initial denitrifying step, an intermediate sulfate reduction step and a subsequent methanogenic step. A fourth, aerobic step may also be included. Mixed hazardous waste 1 is moved sequentially through the process by means of gravity or pump 19.

In the first process step, biological denitrification occurs in first reactor 2. Conditions are created whereby nitrate (or a nitrogenous oxide formed from it by reduction) serves as the terminal electron acceptor. Oxygen is excluded so as to create an anoxic environment. In most cases, if the waste stream does not contain nitric acid, addition of sodium nitrate 3 (with the nitrate ($NO_3$) concentration of the reactor controlled by a nitrate-specific electrode) is necessary. If they are not present in the waste stream, certain trace elements such as molybdenum, copper, iron and manganese are provided as they are required for denitrifiers to produce necessary enzymes.

From reaction stoichiometries presented in the report referenced above, the following nitrate requirements are predicted if addition of a supplemental electron acceptor is necessary:

| Electron donor | Nitrate requirement | |
| --- | --- | --- |
| | Moles of $NO_3$ required per mole of electron donor | Grams of $NO_3$ required per gram of electron donor |
| Benzene | 6.0 | 4.8 |
| Toluene | 7.2 | 4.9 |
| Ethylbenzene | 8.4 | 4.9 |
| Xylenes | 8.4 | 4.9 |
| Phenol | 5.6 | 4.9 |
| Cresols | 8.8 | 3.9 |

The above information on nitrate requirements can be used to determine an appropriate amount of nitrate ion to add to first reactor 2 to enrich denitrifying bacteria therein without enriching denitrifying bacteria in downstream reactors.

The following electron donors can be metabolized (oxidized) under denitrifying conditions:

| Substrate | Product |
| --- | --- |
| Benzene | Unknown |
| Toluene | $CO_2$ |
| Ethylbenzene | Unknown |
| o-Xylene | Unknown |
| m-Xylene | $CO_2$ |
| p-Xylene | Unknown |
| Phenol | $CO_2$ |
| p-Cresol | $CO_2$ |

Metabolism of these substrates also occurs in a denitrifying continuous culture grown on methanol or acetate as the primary electron donor 4. If acetate or methanol is used as an electron donor for denitrification and some remains in the effluent, it is converted to methane in a downstream methanogenic reactor. It has been reported that polychlorinated biphenyls (PCBs) dechlorination rates are greatest with amendment with methanol, glucose and acetone and least with amendment with acetate.

Denitrifying reactions produce alkalinity and tend to increase the pH of the reactor contents. About 3.57 grams of alkalinity are formed for each gram of nitrate-nitrogen ($NO_3$—N) that is denitrified.

This natural consequence of denitrification is used to accomplish two hazardous waste remediation functions. If waste stream 1 is acidic (as many DoD waste streams are), first reactor 2 is operated as a "pH-stat" wherein waste 1 is added to first reactor 2 at the rate required to maintain the appropriate pH within the reactor.

A second function is to provide an environment wherein precipitation of heavy metals present in waste stream 1 can be caused to occur. Denitrification can occur over a pH range of 5–10 and is most effective at pH 7–8.5. At pH 8.5, for example, the solubility of various metal hydroxides 5 is as follows (neglecting complex formation):

| Metal | Solubility, mg/l |
| --- | --- |
| Copper | 0.004 |
| Zinc | 0.04 |
| Iron ($Fe^{++}$) | 3.0 |

This is feasible because denitrifying bacteria are not unusually sensitive to heavy metals or to chlorinated hydrocarbons.

Nitrogen gas 6 produced by biological denitrification is removed from first reactor 2. The first liquid effluent 7 from first reactor 2 is introduced into second reactor 8.

In second reactor 8, biological sulfate reduction occurs in that conditions are created whereby sulfate serves as the primary terminal electron acceptor. If the waste stream does not contain sulfate (which is a common waste constituent derived from sulfuric acid), addition of sodium sulfate 9 (or sulfuric acid) is necessary. An anaerobic environment is maintained automatically by the culture's production of hydrogen sulfide. Reductive dechlorination produces ethylene 15 and other breakdown products.

From the reaction stoichiometries presented in the report referenced above, the following sulfate 9 requirements are predicted if addition of an electron acceptor is necessary:

| Electron donor | Sulfate requirement | |
| --- | --- | --- |
| | Moles of $SO_4^{-2}$ required per mole of electron donor | Grams of $SO_4^{-2}$ required per gram of electron donor |
| Benzene | 3.75 | 4.61 |
| Toluene | 4.50 | 4.69 |
| Ethylbenzene | 5.25 | 4.75 |
| Xylenes | 5.25 | 4.75 |
| Phenol | 3.50 | 3.57 |
| Cresols | 4.25 | 3.78 |

The above information on sulfate requirements can be used to determine an appropriate amount of sulfate ion to add to second reactor 8 to enrich sulfate-reducing bacteria therein without enriching sulfate-reducing bacteria in downstream reactors.

Degradation of aromatic hydrocarbons such as p-cresol occurs under sulfate-reducing conditions. Free energy considerations indicate that degradation of other such compounds, such as toluene and phenol, is favorable thermodynamically. If methanol is added in the denitrification step, some of the excess methanol present in the effluent from first reactor 2 is metabolized in second reactor 8.

Applicant Robert M. Hunter has shown that the initial sulfate stage of a two-stage anaerobic process can be used to effectively reduce heavy metal concentrations to very low levels. This is possible because metal sulfides 10 are much less soluble than metal hydroxides 5. It should be noted that the availability of excess dissolved sulfide in the reactor effectively prevents copper, the heavy metal most toxic to sulfate-reducing bacteria, from reaching the concentration (0.25 to 0.29 percent) required to inhibit sulfate reduction.

If the excess hydrogen sulfide ($H_2S$) produced during sulfate reduction is removed from the reactor (by purging with nitrogen or otherwise), the pH of the solution is increased. There are a variety of ways to recover sulfur from such streams, including a biotechnology (see U.S. Pat. No. 4,666,852). Thus, sulfate-reduction reactor 8 could be operated as a pH-stat by adding an acidic waste stream to the reactor at the rate necessary to maintain a constant, neutral pH. Because both denitrification and sulfate reduction can effectively increase the pH of a waste stream, a balance between the two steps would be necessary.

Second liquid effluent 11 is delivered to third reactor 12. In third reactor 12, dehalogenation (e.g., dechlorination) and methanogenic reactions occur. A significant amount of dechlorination may not occur in the denitrifying reactor, but would occur under methanogenic conditions as a result of cometabolism of a primary substrate 13.

The end products of methanogenesis are methane 14 and carbon dioxide. The end product of dechlorination of PCE and TCE is ethylene 15, a non-hazardous gas. If PCE or TCE is present in mixed hazardous waste 1, reactor 12 contents are degassed to ensure that ethylene 15 does not reach high enough levels to inhibit methanogenesis. Methane formation by *Methanosarcina barkeri* and *Methanothrix soehngenii* is reversibly inhibited by 50 percent at a 3.6–7.2 $\mu$M ethylene (ethene) concentration in the aqueous phase. When ethylene 15 is removed by purging with an inert gas such as nitrogen ($N_2$) or by imposing a vacuum on the headspace 20 of third reactor 12, no inhibition occurs. Sulfate reduction is not impaired by ethylene. Ethylene can be oxidized by aerobic bacteria. Both methane and ethylene may be burned to produce heat for the process or otherwise used beneficially.

In an alternative embodiment, at least a portion of the methanogenic process step occurs underground. In this embodiment, at least a portion of third reactor 12 is the pore space of an underground formation. Methanogenesis occurs in biofilms enriched in that environment.

The estimates of $\mu_{max}$ for mineralization of aromatic hydrocarbons developed in the report referenced above indicate that kinetic control can be used to separate the denitrification step, the sulfate-reduction step and the methanogenic step. Separation would occur with reactors operated at the following dilution rates or mean cell residence times at 37 degrees C and pH 7 in a substantially fresh water (non-marine) medium:

| Reactor | Dilution rate, $hr^{-1}$ | Mean cell residence time, hr |
| --- | --- | --- |
| Denitrification | 0.08 | 13 |
| Sulfate reduction | 0.04 | 25 |
| Methanogenesis | 0.02 | 50 |

At other temperatures and pH's, different dilution rates of MCRT's would be appropriate. Different dilution rates or MCRT's can be achieved in the different reactors with the same throughput by providing a different working volume for each reactor. Alternatively, if cell recycle is practiced, different recycle rates can be used to produce different MCRT's. The specific microorganisms that would be enriched in reactors operated as indicated above would also depend on the salinity of the reactor contents. The methanogenic reactor would be populated by a variety of methanogens. *Methanothrix soehngenii*, for example, is aceticlastic and resistant to certain pesticides, including organophosphates, an organochloride and a carbamate. A variety of other methanogens cannot metabolize acetate, but would convert $H_2$ and $CO_2$, formate or methanol to methane.

If the above process steps were used to pretreat wastewater prior to discharge of third liquid effluent 16 to a municipal wastewater system, it is likely that no additional treatment would be required. If fourth liquid effluent 18 must contain very low levels of organics, then a subsequent aerobic treatment step is provided in fourth reactor 17. This could be accomplished in a conventional aerobic treatment process, such as the activated sludge process or the trickling filter process.

Figure 2:
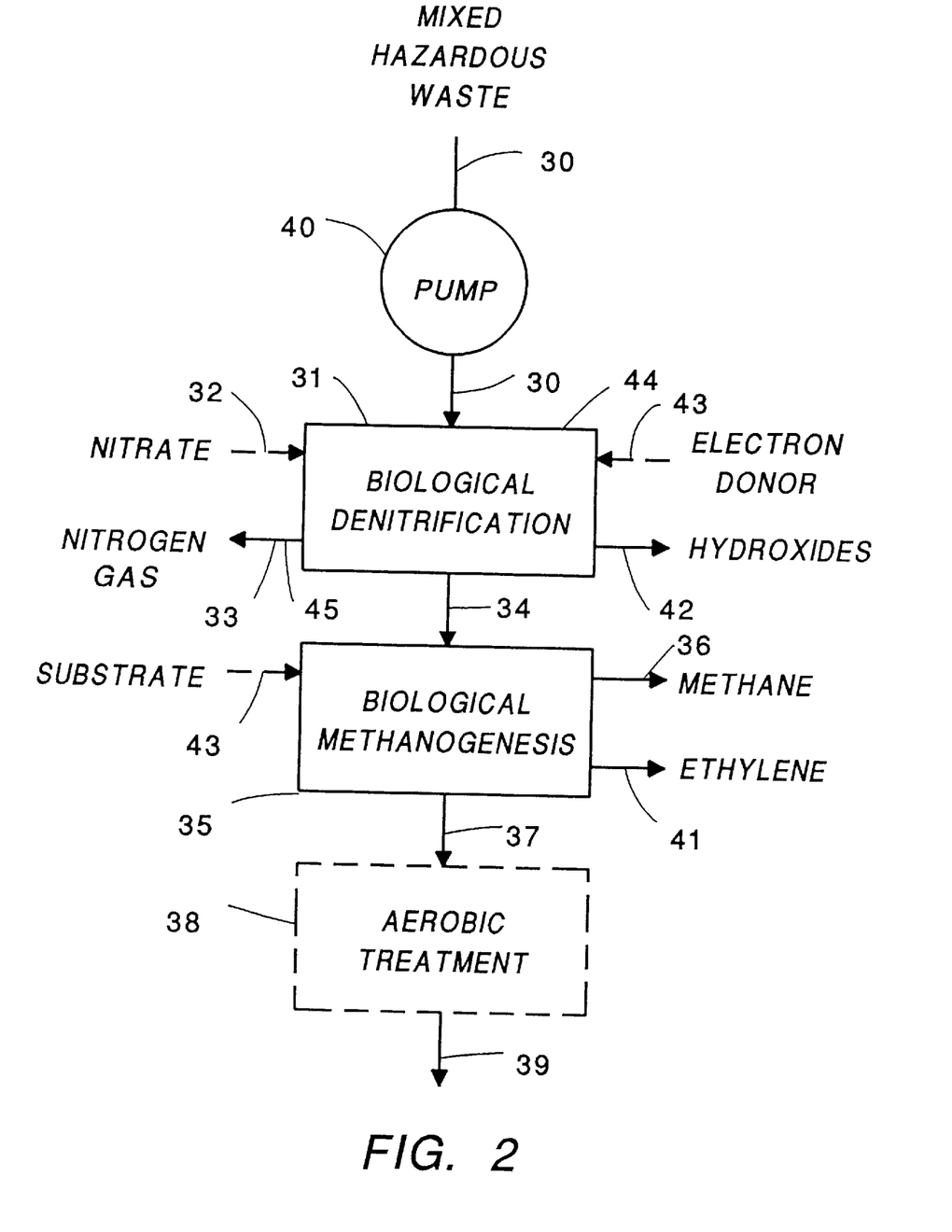
FIG. 2 is a schematic diagram of a second preferred embodiment of the invention.

Reference is now made to FIG. 2 which is a highly schematic block diagram illustrating a second preferred embodiment of the invention, the dashed lines representing possible variations in the process. Mixed hazardous waste 30 is input to the process by pump 40. The process involves an initial denitrifying step and a subsequent methanogenic step, without an intermediate sulfate-reduction step. A third, aerobic processing step may also be included.

Mixed hazardous waste 30 is delivered to first reactor 31 wherein the denitrification step occurs. The denitrification step is operated as explained above for the first preferred embodiment. With first (denitrification) reactor 31 operated as a "pH stat," the target pH would be chosen to optimize both the denitrification and the downstream methanogenesis process steps. For example, unless enrichment of alkaliphilic methanogens that prefer a pH of 8.1 to 9.2 is envisioned, a target pH of about 7.4 would be used.

If necessary, a supplemental electron acceptor, such as nitrate 32, and/or a supplemental electron donor 43, such as methanol, are added to first reactor 31. Metal hydroxides 42 and first liquid effluent 34 are removed from first reactor 31. Nitrogen gas 33 may be removed from first liquid effluent 34 using one of the methods described above. In one embodiment, first reactor 31 includes headspace 44 from which nitrogen gas 33 is removed by vacuum pump 45. Waste nitrogen gas 33 may be scrubbed to remove volatile hydrocarbons contained in it by contacting it with an aqueous waste stream, such as a portion of third liquid effluent 39, which portion is returned to first or second reactor 31 or 35 for further treatment.

First liquid effluent 34 is delivered to second reactor 35 wherein methanogenesis is accomplished. The methanogenic step is operated as noted above in the description of the first preferred embodiment. The microorganisms are grown in either suspended culture or in biofilms and methane 36 and ethylene 41 are produced. Substrate 43, such as methanol, may be added to second reactor 35 to facilitate dechlorination of chlorinated hydrocarbons.

If residual organics concentrations are excessive, a final aerobic treatment step is incorporated into the process. In this case, second liquid effluent 37 is delivered to third reactor 38. Activated sludge and trickling filter unit processes are examples of appropriate aerobic process steps. After treatment, fourth liquid effluent 39 is removed from third reactor 38.

Figure 3:
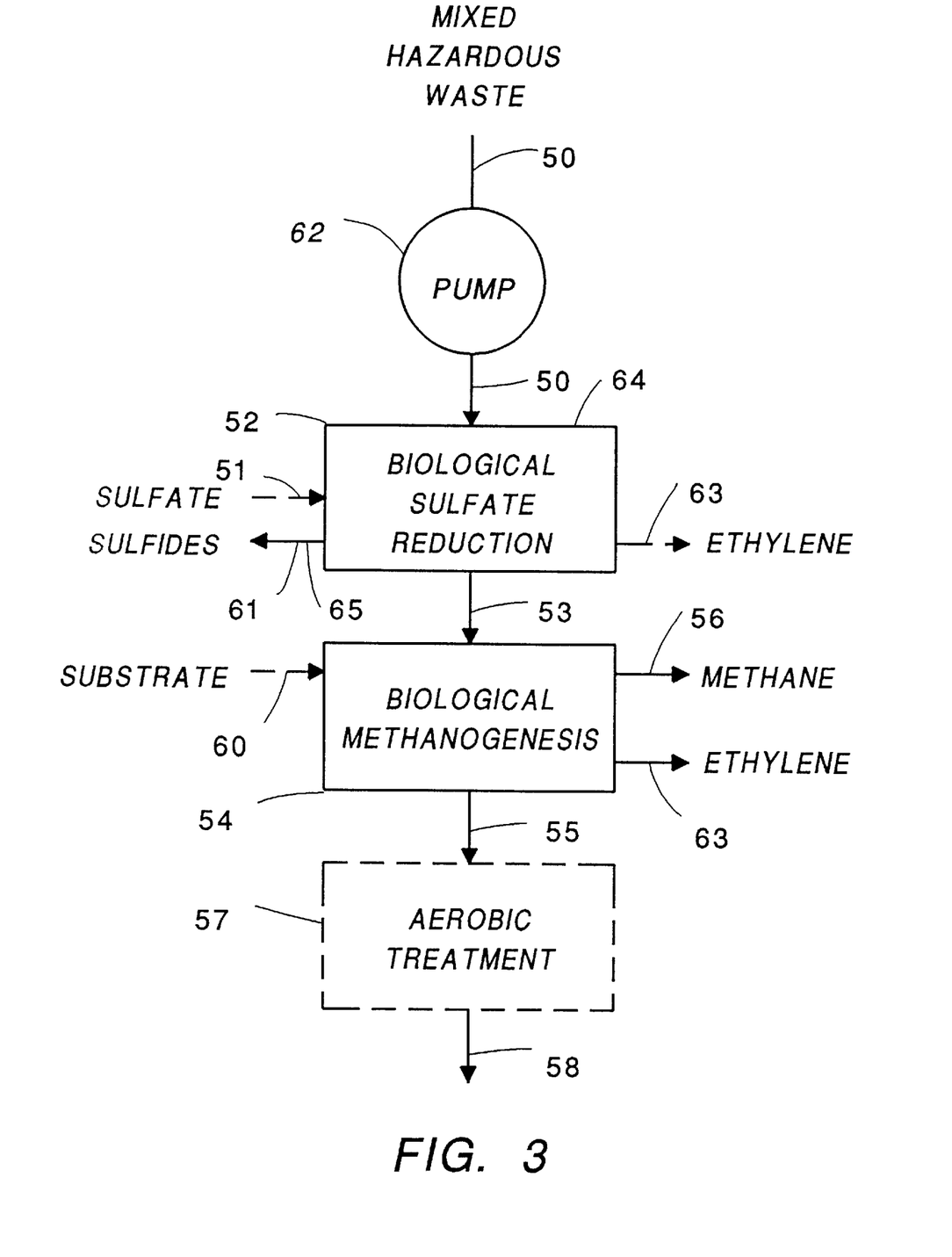
FIG. 3 is a schematic diagram of a third preferred embodiment of the invention.

Reference is now made to FIG. 3 which is a highly schematic block diagram illustrating a third preferred embodiment of the invention, the dashed lines representing possible variations in the process. Mixed hazardous waste 50 is input to the process by pump 62. The process involves an initial sulfate-reduction step and a subsequent methanogenic step. A third, aerobic processing step may also be included.

The initial sulfate-reduction step is accomplished in first reactor 52 which is operated as noted above for the first preferred embodiment. Additional information on process step options is provided in U.S. Pat. No. 5,076,927. Sulfate 51 may be added or it may be present in mixed hazardous waste 50. Hydrogen sulfide gas (e.g., sulfides 61) may be removed from first liquid effluent 53 using one of the methods described above. In one embodiment, first reactor 52 includes headspace 64 from which hydrogen sulfide gas 61 is removed by vacuum pump 65. Waste hydrogen sulfide gas 61 may be scrubbed to remove volatile hydrocarbons contained in it by contacting it with an aqueous waste stream, such as a portion of third liquid effluent 58, which portion is returned to first or second reactor 52 or 54 for further treatment. Biological dechlorination of PCE and TCE will produce ethylene 63.

First liquid effluent 53 of first reactor 52 is transferred to second reactor 54. In a second methanogenic step, dechlorination and methane 56 production occur. Reductive PCE dechlorination by methanogens to produce ethylene 63 during metabolism of a primary substrate 60, such as acetate or methanol, has been documented. Therefore, one such substrate 60 is added to the reactor if one not present in first liquid effluent 53 from the sulfate-reduction step. The specific microorganisms that would be enriched in reactors operated as indicated above would depend on the salinity and temperature of the reactor content. If second reactor 54 is operated at a relatively high pH (above pH 8), over 95 percent of the hydrogen sulfide gas is ionized. At pH 7, about two thirds is ionized. Ionized (soluble) sulfides 61 concentrations over 200 milligrams per liter (as sulfur) are toxic to methanogens.

If residual organics concentrations are excessive, a final aerobic treatment step can be incorporated into the process by transferring second liquid effluent 55 to third reactor 57. Activated sludge and trickling filter unit processes are examples of appropriate aerobic process steps for producing third liquid effluent 58.

Applicants have discovered a novel and unobvious new use for the processes claimed in the U.S. Pat. No. 5,076,927 of one of them. In the referenced patent, methods for culturing microorganisms, and, specifically, for culturing sulfate-reducing bacteria and methane-producing bacteria in at least two reactors in series, are disclosed. The invention in the referenced patent provides a method for neutralizing and removing metals and sulfate from acid mine drainage and other acidic metal sulfate solutions. Sulfate is used as the sole electron acceptor in the biological reduction process. The electron donors are volatile acids or their disassociation products, such as propionic acid, propionate ion, butyric acid, butyrate ion, lactic acid and lactate ion.

Applicants have discovered that the methods in the referenced patent can be used to biologically oxidize aromatic hydrocarbons as electron donors and to biologically reduce halogenated hydrocarbons as electron acceptors. The new use is illustrated in FIG. 3. Mixed hazardous waste 50 is the primary input to the process. The method accomplishes at least one function selected from the group consisting of biologically oxidizing aromatic hydrocarbons, and biologically reducing halogenated hydrocarbons, in at least two reactors in series.

A liquid substrate (i.e., mixed hazardous waste 50) comprising a dissolved sulfate 51 and more moles of at least one dissolved electron donor with a molecular weight greater than that of acetic acid (e.g., an aromatic hydrocarbon in mixed hazardous waste 50) than are required by sulfate-reducing bacteria to biologically reduce at least a portion of the dissolved sulfate, are delivered to first reactor 52. The substrate is fermented in first reactor 52 under anaerobic conditions at a pH between about 6 to 8, at a temperature between about 30 degrees C. to 40 degrees C. and at a mean cell residence time less than that required for essentially complete oxidation of acetic acid by sulfate-reducing bacteria at the selected pH and temperature to produce sulfides 61 and first liquid effluent 53. The concentration of the sulfides 61 generated by the fermentation process in the liquid in first reactor 52 is reduced by conventional means 65.

First liquid effluent 53 from first reactor 52 is delivered to second reactor 54. First liquid effluent 53 is fermented in second reactor 54 at a pH of between about 6.8 to 7.4, at a temperature between about 20 degrees to 65 degrees C. and at a mean cell residence time greater than the mean cell residence time required for essentially complete utilization of acetic acid by methane-producing bacteria to produce methane and second liquid effluent 55. Reductive dehalogenation (e.g., dechlorination) occurs in first reactor 52 and in second reactor 54.

Methane 56, ethylene 63 and second liquid effluent 55 are removed from second reactor 54. If necessary, second liquid effluent 55 is delivered to third reactor 57 for aerobic treatment. After aerobic treatment is completed, third liquid effluent 58 is removed from third reactor 57.

Many variations of the invention will occur to those skilled in the art. All such variations within the scope of the claims are intended to be within the scope and spirit of the invention. For example, autotrophic denitrification could be encouraged by routing at least a portion of the hydrogen sulfide gas generated during sulfate reduction to the denitrification reactor. With this embodiment, sulfur would be recycled through the process, with oxidation to sulfate in the denitrification reactor and reduction to sulfide in the sulfate reduction reactor.

We claim:

1. In combination, the steps of:

delivering to a first reactor a hazardous waste comprised of at least one halogenated hydrocarbon, said first reactor being one of a plurality of reactors for treating said hazardous waste, said reactors being connected in series, wherein, by means of kinetic control, a process occurring in said first reactor is denitrification, precipitating metals from said hazardous waste, and providing a downstream reactor wherein an alkane and an alkene are produced biologically.

2. A method of mixed hazardous waste remediation comprising the steps of:

delivering hazardous waste comprising a halogenated hydrocarbon to a first reactor of a plurality of reactors connected in series, wherein, by means of enrichment, the process occurring in said first reactor is a process comprising biological reduction of an oxyanion, increasing the pH of said hazardous waste by means of a process occurring in at least one of said plurality of reactors, and biologically producing a saturated hydrocarbon and an unsaturated hydrocarbon in a second reactor.

3. The method of claim 2 wherein enrichment comprises limiting the concentration of a microbial growth-limiting substrate in said first reactor.

4. The method of claim 2 further comprising:

operating said first reactor as a suspended growth reactor at a mean cell residence time that prevents methanogenesis, and accomplishing aerobic respiration in a third reactor.

5. A method for bioremediation of hazardous wastes comprising the steps of:

delivering to a first reactor a liquid comprising water and mixed hydrocarbons comprising a halogenated hydrocarbon, operating said first reactor under conditions that exclude molecular oxygen, in a mixed condition, at a substantially constant temperature and pH and at a mean cell residence time that enriches bacteria capable of biological reduction of an oxyanion and that washes out methanogenic bacteria to produce a first effluent, delivering said first effluent to a second reactor, operating said second reactor under predetermined conditions that cause methanogenesis and producing a second effluent, wherein at least a portion of said mixed hydrocarbons serves as an electron acceptor under methanogenic conditions.

6. The method of claim 5 further comprising the steps of:

delivering said second effluent and a gas comprising molecular oxygen to a third reactor, and operating said third reactor under conditions that allow aerobic respiration and producing a third effluent.

7. A process for bioremediation of hazardous wastes comprising:
   delivering a liquid substrate to a first reactor, said substrate comprising water and mixed hydrocarbons,
   said first reactor having contents that are anoxic, mixed and at a substantially constant temperature and pH,
   wherein said first reactor is operated at a mean cell residence time that washes out methanogenic bacteria and produces a first effluent, and
   delivering said first effluent to a second reactor that is operated under predetermined conditions that cause methanogenesis and produce a second effluent.

8. A method for bioremediation of hazardous wastes comprising the steps of:
   delivering to a first reactor a liquid comprising water and at least one organic compound selected from the group consisting of
   tetrachloroethylene,
   trichloroethylene, and
   1,1,1-trichloroethane,
   operating said first reactor under conditions that exclude molecular oxygen, as a continuous stirred tank reactor, at a temperature of between 20 degrees C. and 40 degrees C., at a pH of between 7 and 10 and at a mean cell residence time of no more than ten hours, to accomplish biological reduction of an oxyanion and to produce a first effluent and a gas comprising nitrogen,
   delivering said first effluent to a second reactor,
   operating said second reactor under anaerobic conditions, at a pH of between about 6.8 to 7.4, at a temperature between about 20 degrees C. to 65 degrees C. and at a mean cell residence time of at least thirty hours, to produce a second effluent and methane gas,
   removing the methane gas from said second reactor, and
   removing said second effluent from said second reactor.

9. A method for bioremediation of hazardous wastes comprising the steps of:
   delivering to a first reactor a liquid substrate comprising water and at least one organic compound selected from the group consisting of
   tetrachloroethylene,
   trichloroethylene, and
   1,1,1-trichloroethane,
   operating said first reactor under conditions that exclude molecular oxygen, as a completely mixed tank reactor, at a temperature of between 20 degrees C. and 40 degrees C., at a pH of between 7 and 10 and at a mean cell residence time of no more than fifteen hours, to produce a first effluent and a first gas,
   delivering said first effluent to a second reactor,
   operating said second reactor under anaerobic conditions, at a pH of between about 6.8 to 7.4, at a temperature between about 20 degrees C. to 65 degrees C. and at a mean cell residence time of at least thirty hours, to produce a second effluent and methane gas,
   removing the methane gas from said second reactor, and
   removing said second effluent from said second reactor.

10. The method of claim 9 further comprising:
    providing a headspace in said first reactor, and
    removing said first gas from said first reactor.

11. In combination, the steps of:
    delivering a mixed hazardous waste comprising at least one halogenated hydrocarbon to a first reactor,
    practicing biological kinetic control in said first reactor, said first reactor providing means for biologically reducing at least one oxyanion,
    performing biological methanogenesis and biological reductive dehalogenation in a second reactor, and
    sequentially moving said mixed hazardous waste through said first reactor and then through said second reactor.

12. The process of claim 11 wherein said at least one oxyanion is dissolved nitrate.

13. The process of claim 11 wherein said at least one oxyanion is dissolved nitrite.

14. A method of hazardous waste bioremediation comprising the steps of:
    enriching a culture capable of biological reduction of an oxyanion in a reactor having a content by providing a stoichiometric amount of a compound from the group consisting of:
    an oxyanion, and
    an electron donor,
    wherein said content comprises a halogenated hydrocarbon, and
    subsequent enriching a methanogenic culture in said reactor by providing a growth substrate of a methanogen.

15. The method of claim 14 wherein said reactor comprises the pore space of a porous underground formation.

16. A method of hazardous waste bioremediation comprising the steps of:
    enriching a denitrifying culture in a reactor having a content by providing a stoichiometric amount of a compound from the group consisting of:
    an electron acceptor for denitrification, and
    an electron donor for denitrification,
    wherein said content comprises a hazardous waste, and
    subsequently enriching a methanogenic culture in said reactor by providing a growth substrate of a methanogen.

17. A process for mixed hazardous waste remediation comprising:
    delivering hazardous waste comprising a halogenated hydrocarbon to a first reactor of a plurality of reactors connected in series,
    wherein, by means of kinetic control, the process occurring in said first reactor is a process comprising biological reduction of an oxyanion, and
    biologically producing an alkane in a second, downstream reactor,
    wherein at least a component of said hazardous waste serves as an electron acceptor.

18. A process for mixed hazardous waste remediation comprising:
    delivering hazardous waste comprising a halogenated hydrocarbon to a first reactor of a plurality of reactors connected in series,
    wherein, by means of enrichment, the process occurring in said first reactor is a process comprising biological reduction of an oxyanion, said process producing a first effluent,
    increasing the pH of said hazardous waste by means of a process occurring in at least one reactor,
    delivering said first effluent to a second, downstream reactor, and
    biologically producing a saturated hydrocarbon and an unsaturated hydrocarbon in said second, downstream reactor.

19. The process of claim 18 wherein the process occurring in said first reactor comprises limiting the availability of a microbial growth-limiting substrate in said first reactor.

20. The process of claim 18 further comprising:
operating said first reactor at a mean cell residence time that prevents methanogenesis, and
accomplishing aerobic respiration in a final reactor.

21. A process for bioremediation of hazardous wastes comprising:
delivering to a first reactor a substrate comprising water and mixed hydrocarbons comprising a halogenated hydrocarbon,
operating said first reactor under conditions that substantially exclude molecular oxygen, in a mixed condition, at a substantially constant temperature and pH and at a mean cell residence time that enriches bacteria capable of biological reduction of an oxyanion and that substantially washes out methanogenic bacteria to produce a first effluent,
delivering said first effluent to a second reactor,
operating said second reactor under predetermined conditions that support methanogenesis and producing a second effluent,
wherein at least a portion of said mixed hydrocarbons serves as an electron acceptor under methanogenic conditions.

22. The process of claim 21 further comprising:
delivering said second effluent and a gas comprising molecular oxygen to a third reactor, and
operating said third reactor under conditions that support aerobic respiration, and
producing a third effluent.

23. A process for bioremediation of hazardous wastes comprising:
delivering to a first reactor a substrate comprising water and at least one organic compound selected from the group consisting of
tetrachloroethylene,
trichloroethylene, and
1,1,1-trichloroethane,
operating said first reactor under conditions that exclude molecular oxygen, as a continuous stirred tank reactor, at a temperature of between 20 degrees C. and 40 degrees C., at a pH of between 7 and 10 and at a mean cell residence time of no more than ten hours, to accomplish biological reduction of an oxyanion and to produce a first effluent and a gas comprising nitrogen,
delivering said first effluent to a second reactor,
operating said second reactor under anaerobic conditions, at a pH of between about 6.8 to 7.4, at a temperature between about 20 degrees C. to 65 degrees C. and at a mean cell residence time of at least thirty hours, to produce a second effluent and methane gas,
removing the methane gas from said second reactor, and
removing said second effluent from said second reactor.

24. A method of mixed hazardous waste remediation comprising the steps of:
delivering hazardous waste comprising a halogenated hydrocarbon to a first reactor of a plurality of reactors connected in series,
wherein, by means of kinetic control, the process occurring in said first reactor is a process comprising biological reduction of an oxyanion, and
biologically producing an alkane in a second reactor,
wherein at least a component of said hazardous waste serves as an electron acceptor.

25. The method recited in claim 24 wherein the mixed waste delivery step comprises delivering a mixed waste stream containing a second hydrocarbon and said first treatment step comprises metabolizing at least a portion of said second hydrocarbon.

26. The method recited in claim 24 wherein said first biological treatment comprises a biological denitrification step.

27. The method recited in claim 26 wherein said oxyanion is an oxide of nitrogen.

28. A method of mixed hazardous waste remediation comprising:
a mixed waste delivery step wherein a mixed waste stream comprising a hazardous hydrocarbon is delivered to a reactor;
a first treatment step wherein said waste stream is subjected to a first biological treatment by metabolizing at least a portion of the hazardous hydrocarbon during the reduction of at least a portion of an oxyanion to produce a breakdown product; and
a second treatment step wherein said treated waste stream is subjected to a second biological treatment step by metabolizing at least a portion of the breakdown product and producing an alkane.

29. The method recited in claim 28 wherein the mixed waste delivery step comprises delivering a mixed waste stream containing a halogenated hydrocarbon, said second treatment step comprises dehalogenating at least a portion of said halogenated hydrocarbon.

30. The method recited in claim 29 wherein the mixed waste delivery step comprises delivering a mixed waste stream containing a second hydrocarbon and said first treatment step comprises metabolizing at least a portion of said second hydrocarbon.

31. A method of treatment of a hazardous waste comprising:
treating the waste initially in a first environment having conditions appropriate for biological reduction of an oxyanion, and
then treating the waste in a second environment having conditions appropriate for a biological process that requires a lower or more negative oxidation-reduction potential than said first environment.

32. The method of claim 31 wherein the oxyanion is an oxide of nitrogen.

33. The method of claim 31 wherein said second environment is a methanogenic environment.

34. The method of claim 31 further comprising subsequently treating the waste in a third, aerobic environment.

* * * * *